United States Patent
Horny et al.

(10) Patent No.: US 11,713,481 B2
(45) Date of Patent: Aug. 1, 2023

(54) PROCESS FOR DETECTING NUCLEIC ACID MOLECULES BY MAGNETIC HYPERTHERMIA AND ASSEMBLY ENABLING SUCH DETECTION

(71) Applicants: Centre National de la Recherche Scientifique (CNRS), Paris (FR); Institut National de la Sante et de la Recherche Medicale (INSERM), Paris (FR); Sorbonne Universite, Paris (FR)

(72) Inventors: Marie-Charlotte Horny, Paris (FR); Jean-Michel Siaugue, Choisy-le-Roi (FR); Vincent Dupuis, Paris (FR); Mathieu Lazerges, Paris (FR); Jean Gamby, Saclay (FR)

(73) Assignees: Centre National de la Recherche Scientifique (CNRS), Paris (FR); Institut National de La Sante et de la Recherche Medicale (INSERM), Paris (FR); Sorbonne Universite, Paris (FR)

(*) Notice: Subject to any disclaimer, the term of this patent is extended or adjusted under 35 U.S.C. 154(b) by 519 days.

(21) Appl. No.: 16/753,404

(22) PCT Filed: Oct. 5, 2018

(86) PCT No.: PCT/EP2018/077080
§ 371 (c)(1),
(2) Date: Apr. 3, 2020

(87) PCT Pub. No.: WO2019/068844
PCT Pub. Date: Apr. 11, 2019

(65) Prior Publication Data
US 2020/0263241 A1    Aug. 20, 2020

(30) Foreign Application Priority Data
Oct. 5, 2017    (FR) ..................... 1759346

(51) Int. Cl.
*C12Q 1/6834*    (2018.01)
*C12Q 1/6825*    (2018.01)

(52) U.S. Cl.
CPC ......... *C12Q 1/6834* (2013.01); *C12Q 1/6825* (2013.01); *C12Q 2523/305* (2013.01); *C12Q 2527/107* (2013.01); *C12Q 2563/116* (2013.01); *C12Q 2563/143* (2013.01); *C12Q 2563/155* (2013.01); *C12Q 2565/607* (2013.01); *C12Q 2565/629* (2013.01)

(58) Field of Classification Search
CPC ............... C12Q 1/6834; C12Q 1/6825; C12Q 2523/305; C12Q 2527/107; C12Q 2563/116; C12Q 2563/143; C12Q 2563/155; C12Q 2565/607; C12Q 2565/629

See application file for complete search history.

(56) References Cited

U.S. PATENT DOCUMENTS

| 6,506,564 | B1 | 1/2003 | Mirkin et al. |
| 2005/0100930 | A1 | 5/2005 | Wang et al. |
| 2009/0227044 | A1* | 9/2009 | Dosev .............. G01N 33/54333 436/526 |
| 2011/0008797 | A1* | 1/2011 | Zilch ........................ B01L 7/52 977/902 |
| 2013/0154671 | A1 | 6/2013 | Lee et al. |

OTHER PUBLICATIONS

Lacroix et al, A frequency-adjustable electromagnet for hyperthermia measurements on magnetic nanoparticles, 2008, Review of Scientific Instruments 79, 093909, 1-8. (Year: 2008).*
Dec. 22, 2017 (FR) French Search Report FR 1759346.
Nov. 2, 2018 (WO) International Search Report PCT/JP2018/077080.
Fratila et al. "Nucleic Acid-based Engineering of Iron Oxide Nanoparticles for Magnetic Hyperthermia Applications" XI Simposio de Investogadores Joveness RSEQ—Sigma Aldrich. Dec. 4, 2014.
Dias et al. "DNA as a Molecular Local Thermal Probe for the Analysis of Magnetic Hyperthermia". Angewandte Chemie International Edition, vol. 52, No. 44. Oct. 25, 2013. pp. 11526-11529.
Horny et al. (2016), "Electrochemical DNA biosensors based on long-range electron transfer: investigating the efficiency of a fluidic channel microelectrode compared to an ultramicroelectrode in a two-electrode setup" Lab on a Chip, 16(22), 4373-4381.
Lamer et al. Theory, production and mechanism of formation of monodispersed hydrosols, 1950, Journal of the American Chemical Society, 72(11), 4847-4854.

* cited by examiner

*Primary Examiner* — Narayan K Bhat
(74) *Attorney, Agent, or Firm* — Banner & Witcoff, Ltd.

(57) ABSTRACT

A process for pre-concentration and detection of at least one single-stranded nucleic acid target molecule, the process comprising the steps of generating a flow of liquid comprising at least one magnetic nanoparticle in a micro-channel and a plurality of single-stranded nucleic acid probe molecules attached to the nanoparticle, generating an alternating magnetic field in the part of the micro-channel using an electromagnet, the magnetic field having an intensity and frequency that are suitable for causing magnetic hyperthermia of the nanoparticles so as to cause denaturing of the duplex formed by the single-stranded nucleic acid target molecule and the single-stranded nucleic acid probe molecule, and detecting the single-stranded target molecule dispersed in the liquid.

19 Claims, 5 Drawing Sheets

PROCESS FOR DETECTING NUCLEIC ACID MOLECULES BY MAGNETIC HYPERTHERMIA AND ASSEMBLY ENABLING SUCH DETECTION

RELATED APPLICATION DATA

This application is a National Stage Application under 35 U.S.C. 371 of co-pending PCT application number PCT/EP2018/077080 designating the United States and filed Oct. 5, 2018; which claims the benefit of FR application number 1759346 and filed Oct. 5, 2017 each of which are hereby incorporated by reference in their entireties.

FIELD OF THE INVENTION

The invention concerns a process for detecting one or more single-stranded nucleic acid molecules such as DNA or RNA from a sample to be tested, and the implementation of this detection by using a biosensor.

STATE OF THE ART

The identification of specific markers for certain types of cancers and infectious diseases can permit early, inexpensive, reliable and fast diagnosis of a targeted disease. Some nucleic acids, for example some RNAs, for example some microRNAs, are known disease markers. For example, the quantitative detection of micro-RNA-122 in a sample to be tested could permit diagnosing liver diseases such as hepatitis B and C, as well as drug-induced diseases.

To detect low concentrations of nucleic acid molecules, for example, femtomolar concentrations, the following is known:

- implementing an amplification reaction specific for one or more nucleic acid molecules to be tested. The specific amplification reaction is done, for example, by polymerase chain reaction (PCR), loop-mediated isothermal amplification (LAMP) or recombinase polymerase amplification (RPA);
- detecting the amplification product. For example, it is known to detect the amplification product by using DNA chips.

However, the use of PCR requires time: several temperature-conditioning cycles are necessary to amplify the targeted DNA or RNA. Moreover, PCR, LAMP or RPA-type amplification techniques may lead to quantification errors limiting the precision of the diagnosis issued as a result of the detection, in particular when amplifying RNA molecules comprising around ten bases.

To this end, it is known to use so-called direct detection techniques, not requiring the amplification step, to detect and/or quantify the nucleic acid target molecules. In particular, the use of electrochemical detection techniques is known. Horny et al. (Horny, M. C., Lazerges, M., Siaugue, J. M., Pallandre, A., Rose, D., Bedioui, F., ... & Gamby, J. (2016), *Electrochemical DNA biosensors based on long-range electron transfer: investigating the efficiency of a fluidic channel microelectrode compared to an ultramicroelectrode in a two-electrode setup*, Lab on a Chip, 16(22), 4373-4381) describe the use of a system comprising two electrodes arranged in a micro-channel to detect a target microRNA in solution in the micro-channel. At least one of the electrodes comprises a self-assembled monolayer of nucleic acid probe molecules. The hybridization of one or more RNA strands allows running a faradic current in the presence of a redox couple in the solution. This system allows detecting very low concentrations of RNA, for example, greater than an attomole.

However, the concentration in target molecules measured may be very dependent on diffusion phenomena upstream of detection or phenomena of adsorption of the target molecules, for example on the walls of the conduits that transport the target molecules to the electrodes. These effects are amplified when the concentrations in target molecules are low, and when the ratio between the wall surface and the volume of liquid used increases.

SUMMARY OF THE INVENTION

One objective of the invention is to propose a solution to detect a quantity of nucleic acids present in a sample to be tested, including a very low concentration, for example around an attomole, by limiting or preventing errors caused by the effects of diffusion and/or adsorption of the nucleic acids to be tested before the detection thereof.

This objective is reached in the context of the present invention by means of a detection process for at least one single-stranded nucleic acid target molecule, the process comprising the steps of:

a) generating a flow of liquid comprising at least one magnetic core-shell type nanoparticle in a micro-channel of a microsystem, and a plurality of single-stranded nucleic acid probe molecules attached to nanoparticle, each single-stranded nucleic acid probe molecule being designed to be at least partially hybridized to a single-stranded nucleic acid target molecule by forming a duplex, at least a part of the micro-channel being arranged in the gap of an electromagnet;

b) generating an alternating magnetic field in part of the micro-channel by means of an electromagnet, the alternating magnetic field having an appropriate intensity and frequency to cause magnetic hyperthermia in nanoparticles so as to induce denaturation of the duplex formed by the single-stranded nucleic acid probe molecule and by the single-stranded nucleic acid target molecule;

c) detecting the single-stranded target molecule dispersed in the liquid.

Since the single-stranded nucleic acid target molecules are transported via the magnetic nanoparticles by the flow to a detector, the effects of uncontrolled adsorption and diffusion are avoided. This permits detecting a concentration of single-stranded nucleic acid target molecules with better precision.

Moreover, since denaturation is implemented by magnetic hyperthermia, it is possible to denature the duplexes while maintaining and/or limiting a mean temperature of the liquid to avoid denaturing other biological compounds in solution in the liquid, in particular, by controlling the liquid at a physiological temperature.

The invention is advantageously supplemented by the following characteristics, taken individually or in any one of the technically-possible combinations thereof:

- the micro-channel has a geometry and flow of liquid with a mean speed such that the nanoparticle(s) are transported for more than 8 seconds on average in part of the micro-channel;
- the width $W_{ag}$ of the gap is less than 5 mm;
- the nanoparticle comprises a core of ferromagnetic or ferrimagnetic material and a shell of silica surrounding the core;
- the core of the nanoparticle is maghemite;

the core of the nanoparticle has a length and width, and the mean length of the core of the nanoparticle is greater than 20 nm;

the core of the nanoparticle(s) comprises an aggregate of ferromagnetic or ferrimagnetic nuclei, the aggregate comprising on average at least two nuclei;

the mean length-to-width ratio of the nanoparticles is greater than 1.5;

the melting temperature of duplex is designed so that strictly more than the majority of duplexes are denatured during step b) of the process;

step c) of detecting the single-stranded target molecule dispersed in the flow is implemented by electrochemistry by imposing an electrical potential difference between two electrodes, the electrodes being partly arranged in the micro-channel;

at least one electrode couple comprising a working electrode and a counter-electrode, is arranged in the micro-channel, downstream of the part of the micro-channel arranged in the gap of electromagnet, in the direction of flow;

the single-stranded nucleic acid probe molecules are attached to a surface of one of the electrodes, said single-stranded molecules being designed to be at least partially hybridized to the single-stranded nucleic acid target molecule(s);

one of the electrodes comprises at least one thin layer chosen from among a thin gold layer, a thin platinum layer and a thin carbon layer;

the liquid comprise a redox intercalator for the duplex and a redox compound couple;

the process comprises a step prior to step a) in which the nanoparticle(s) provided with single-stranded nucleic acid probe molecules are mixed with a sample to be tested: since the single-stranded nucleic acid target molecules are pre-concentrated on the surface of magnetic nanoparticles during mixing with the test sample, it is possible to detect a concentration of single-stranded nucleic acid target molecules with better precision.

Another object of the invention is an assembly for detecting at least one single-stranded nucleic acid target molecule, the assembly comprising:

an electromagnet with an gap, a micro-channel in which a liquid can flow, the micro-channel comprising at least one part arranged in the gap of electromagnet, at least one magnetic nanoparticle of the core-shell type, and a plurality of single-stranded nucleic acid probe molecules attached to the nanoparticle, each single-stranded nucleic acid probe molecule being designed to be at least partially hybridized to a single-stranded nucleic acid target molecule by forming a duplex, the electromagnet being able to generate an alternating magnetic field with an appropriate intensity and frequency to cause magnetic hyperthermia of the nanoparticle(s) when the nanoparticle(s) are transported by the liquid into the part of the micro-channel arranged in the gap of electromagnet, so as to induce a denaturation of the duplex formed by the single-stranded nucleic acid probe molecule and the single-stranded nucleic acid target molecule.

The invention is advantageously supplemented by the following characteristics, taken individually or in any one of the technically-possible combinations thereof:

the assembly also comprises at least two electrodes arranged at least partially in the micro-channel, a voltage difference between the electrodes being able to be controlled to detect the single-stranded target molecule dispersed in the flow by electrochemistry;

the assembly comprises single-stranded nucleic acid probe molecules attached to a surface of one of the electrodes, said single-stranded molecules being designed to be at least partially hybridized to the single-stranded nucleic acid target molecule(s);

one of the electrodes comprises at least one thin layer chosen from among a thin gold layer, a thin platinum layer and a thin carbon layer.

Another object of the invention is a magnetic nanoparticle of the core-shell type comprising a core of ferromagnetic or ferrimagnetic material and a silica shell surrounding the core, in which the core of the nanoparticle has a length and a width, and in which the length of the core of the nanoparticle is greater than 20 nm.

The invention is advantageously supplemented by the following characteristics, taken individually or in any one of the technically-possible combinations thereof:

the core is maghemite;

the core comprises an aggregate of ferromagnetic or ferrimagnetic nuclei, the aggregate comprising at least three nuclei;

the length-to-width ratio of the nanoparticle is greater than 1.5;

the nanoparticle is combined with a plurality of single-stranded nucleic acid probe molecules attached to the nanoparticle;

Another object of the invention is the manufacturing process for magnetic nanoparticles of the core-shell type comprising a core of ferromagnetic or ferrimagnetic material and a silica shell surrounding the core, comprising the steps of:

a) formation of an aggregate of a plurality of nuclei of ferromagnetic or ferrimagnetic material, by dispersion of the nuclei in a saline solution, so as to obtain the core;

b) encapsulation of the core in the silica shell.

Advantageously, the saline solution has an ionic force greater than or equal to 1 mM.

PRESENTATION OF THE DRAWINGS

Other characteristics and advantages will appear from the following description, which is purely illustrative and non-limiting and should be read with regard to the attached figures, in which.

Figure 15:
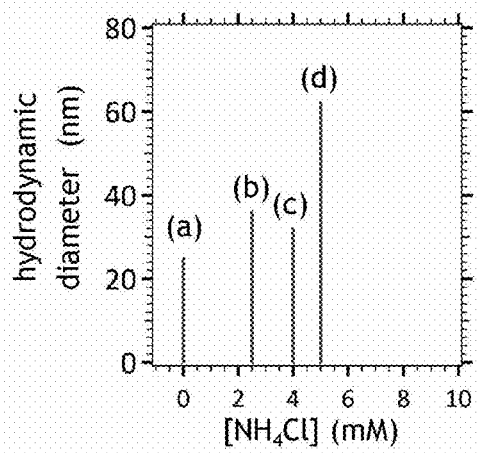
Figure 16:
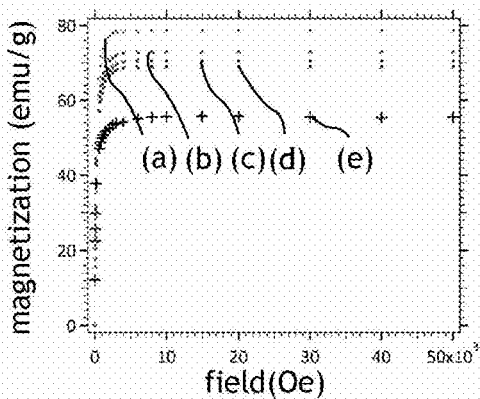
Figure 17:
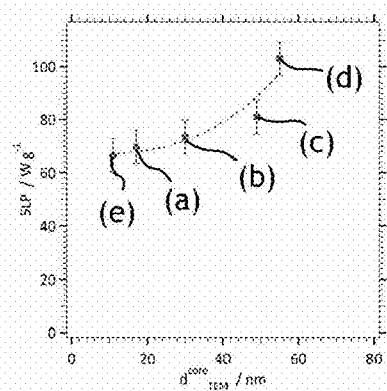
Figures 18, 19:
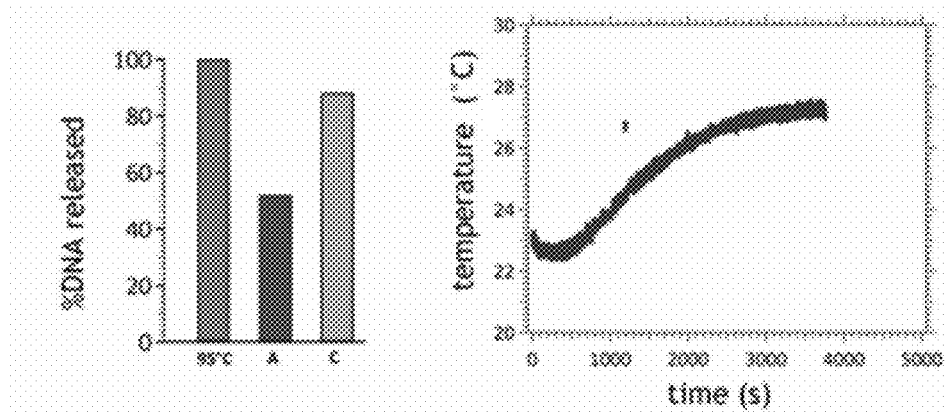
Figures 20, 21:
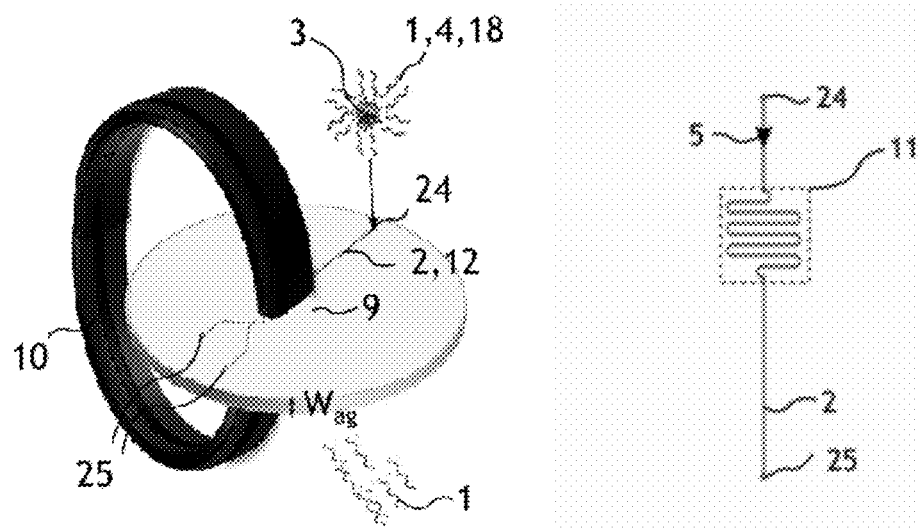
Figure 22:
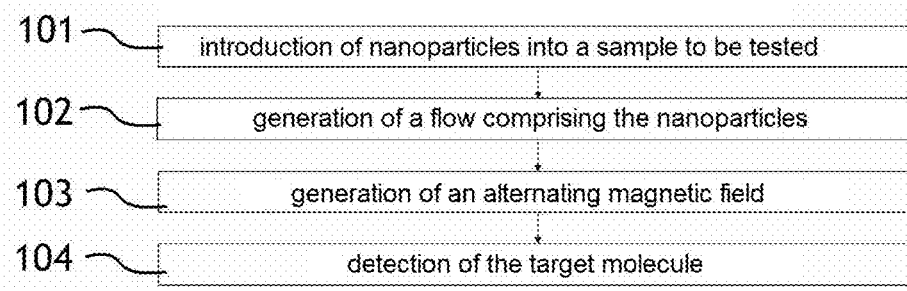
Figure 23:
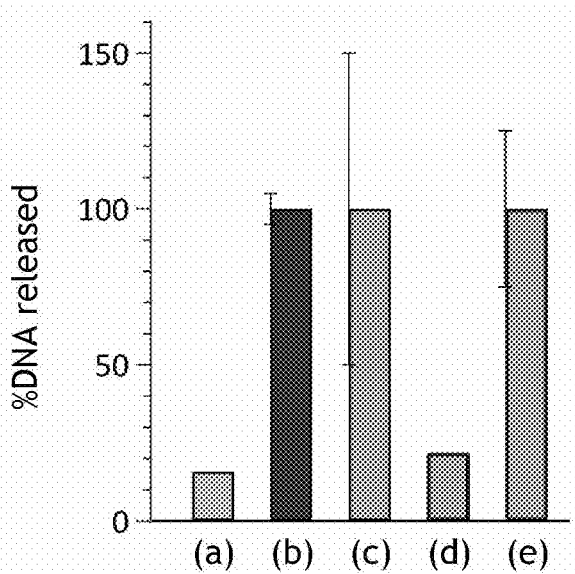
Figure 24:
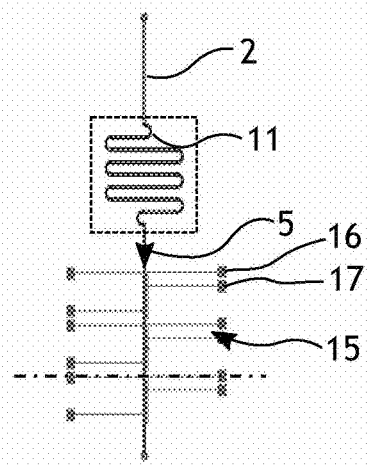
Figure 25:
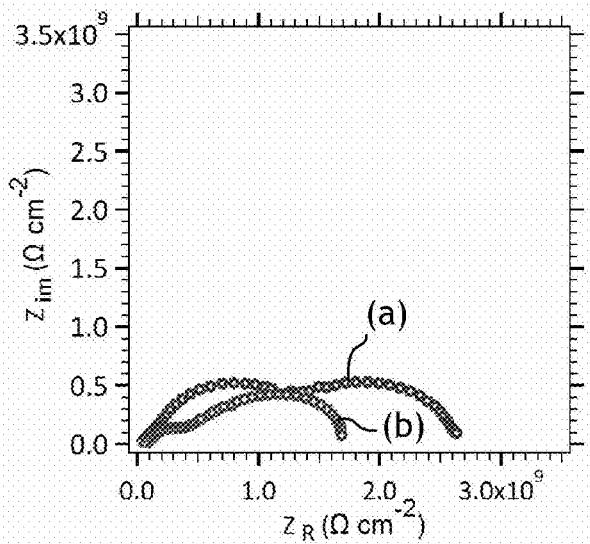

FIG. 15 comparatively illustrates the hydrodynamic diameter of several types of magnetic nanoparticles;

FIG. 16 comparatively illustrates the magnetization of several types of magnetic nanoparticles;

FIG. 17 comparatively illustrates the heating power of several types of magnetic nanoparticles;

FIG. 18 illustrates the proportion between the quantity of DNA released by the magnetic nanoparticles compared to the quantity of DNA initially present on the magnetic nanoparticles;

FIG. 19 illustrates the change in mean temperature of the liquid during magnetic hyperthermia of the magnetic nanoparticles;

FIG. 20 illustrates an assembly for detecting a single-stranded nucleic acid target molecule;

FIG. 21 illustrates a micro-channel designed for magnetic hypothermia of the magnetic particles on a chip and for the detection of a single-stranded nucleic acid target molecule;

FIG. 22 illustrates a process conforming to the invention;

FIG. 23 illustrates the proportion between the quantity of DNA released by the magnetic nanoparticles compared to the quantity of DNA initially present on the magnetic nanoparticles;

FIG. 24 illustrates a system designed for the electrochemical detection of magnetic nanoparticles;

FIG. 25 illustrates electrochemical detection of DNA.

DEFINITIONS

The "hydrodynamic diameter" of a nanoparticle, or Stokes diameter, in a fluid medium means the $R_H$ value given by the following formula (1):

$$R_H = \frac{k_B T}{6\pi\eta D} \quad (1)$$

Where $k_B$ is the Boltzmann constant, T is the temperature in Kelvin, $\eta$ is the viscosity of the medium, and D the diffusion coefficient of the nanoparticle in the medium. This radius may, for example, be measured by dynamic light scattering (DLS).

The "diameter" or "physical diameter" of a nanoparticle means the diameter observable by imaging the nanoparticle, for example by transmission electron microscopy (TEM).

The "length" l of a nanoparticle 3 means the maximum size of the nanoparticle on a straight line passing through the center of inertia of this nanoparticle.

The "width" w of a nanoparticle 3 means the minimum size of the nanoparticle on a straight line passing through the center of inertia of this nanoparticle.

Generally, any characteristic relating to the size of a nanoparticle, such as length or width, is defined in the "physical" sense, for example, observable by TEM, unless the term hydrodynamic is specified.

"Gap" means a space locally separating two parts of an electromagnet core. The air-gap width $W_{ag}$ means the minimum distance separating these two parts.

The "length" of a channel means the size of a channel along the main direction of fluid flow.

The "width" of a channel means the maximum size of a channel along the transverse direction to the main direction of fluid flow.

The "height" of a channel means the minimum size of a channel in a transverse direction to the main direction of fluid flow.

"Micro-channel" or "microfluidic channel" means a channel comprising at least one entrance and at least one exit, and whose height is less than 500 μm.

DETAILED DESCRIPTION OF ONE EMBODIMENT OF THE INVENTION

Figure 1:
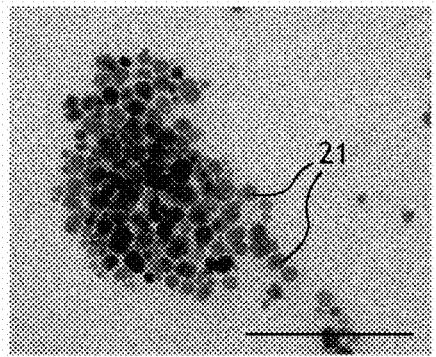
FIG. 1 is a transmission electron microscope image of maghemite magnetic nanoparticles.

In reference to FIG. 1, magnetic nanoparticles of maghemite $\gamma$-$Fe_2O_3$ can be synthesized by the so-called Massart process, from colloidal magnetite. The synthesis to produce nanoparticles illustrated in FIG. 1 comprises a step of inorganic polycondensation, wherein two precursors are formed, $Fe_2(OH)_4$ and $Fe_3(OH)_6$. When the precursor concentration reaches a limit value, magnetite seeds are formed (nucleation) and grow. Seed formation is controlled by the precursor concentration, blocking nucleation when it reaches a lower limit value and leads to the maturation and aging of the seeds. This process is described in detail by LaMer, V. K., & Dinegar, R. H. in *Theory, production and mechanism of formation of monodispersed hydrosols*, 1950, Journal of the American Chemical Society, 72(11), 4847-4854.

The size and shape of the nanoparticles synthesized can be controlled, for lengths less than around 15 nm, by the ratio between the quantity of Fe(II) and Fe(III) and by the temperature, the pH and the nature of the base used. The nanoparticles are then oxidized in an acid medium, leading to the formation of maghemite $\gamma$-$Fe_2O_3$.

The size of the nanoparticles and their surface charge can be characterized by two techniques: dynamic light scattering (DLS) and transmission electron microscopy (TEM).

FIG. 1 is a TEM photograph of an assembly of magnetic nanoparticles synthesized by the method previously described. These nanoparticles are designated by "nuclei" 21. Nitric acid can be introduced into the medium so as to cause larger diameter nuclei 21 to precipitate and thereby filter them. FIG. 1 illustrates nuclei 1 of larger diameters. The scale bar of FIG. 1 has a length of 100 nm.

Figure 2:
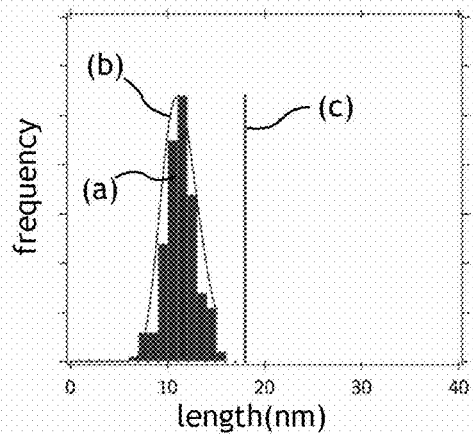
FIG. 2 illustrates the size of the maghemite magnetic nanoparticles.

In reference to FIG. 2, nuclei 21, whose synthesis is described above, has a mean hydrodynamic diameter of 18.1 nm, (measured by DLS) and a mean length $l_0$ of 11 nm. Columns (a) of the histogram are a measurement of the physical length of the sample nanoparticles, curve (b) is an adjustment of the distribution P(l) of nanoparticle length $l_0$ according to a log-normal law, whose parameters are the mean nanoparticle length $l_0$ and standard deviation $\sigma$, according to formula (2):

$$P(l) = \frac{1}{\sqrt{2\pi}\,\sigma l} e^{-\frac{\ln(l/l_0)^2}{2\sigma^2}} \quad (2)$$

Figure 3:
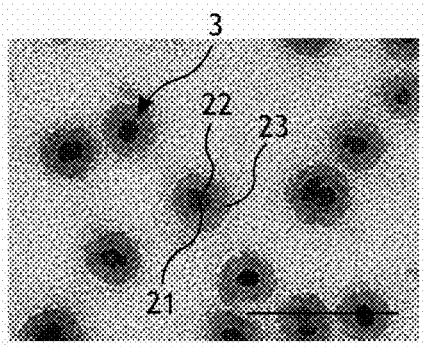
FIG. 3 is a transmission electron microscope image of magnetic nanoparticles comprising a core and a shell.

In reference to FIG. 3, a magnetic nanoparticle 3 conforming to the invention may comprise a core 22 and a shell 23. Core 22 may comprise one or more nuclei 21. Shell 23 may be produced by encapsulation of core 22 of a magnetic nanoparticle 3 in a silica shell 23. Thus, the outer surface of magnetic nanoparticle 3 in silica can be functionalized by known methods, for example by using amine and/or carboxyl groups. Moreover, the silica shell permits screening the dipole interactions of magnetic cores 22. For example, the shell may be produced using a sol-gel process. This process comprises a first step in which a silica monomer is condensed (RSi(OR)$_3$) on the surface of a nucleus 21. It is followed by steps of hydrolysis and condensation in a mixture of water and ethanol. During hydrolysis, silanol groups are formed and produce siloxane groups by intermolecular condensation. A siloxane can be condensed onto a hydroxyl group at the surface of nucleus 21. The silanol groups are then condensed on silica and cross-linked so as to form a silica network. TEOS, added first, initiates the cross-linking of the silica network and facilitates the condensation of APTS and PEOS. The reaction is stopped by introducing ether, which leads to a precipitation of nanoparticles among themselves, by a reduction of the dielectric constant of the reaction medium. The scale bar of FIG. 3 has a length of 100 nm.

Core 22 of a magnetic nanoparticle 3 can generally be produced in a ferromagnetic or ferrimagnetic material. The majority of magnetic nanoparticles 3 illustrated in FIG. 3 have a core comprising a single nucleus 21.

Figure 4:
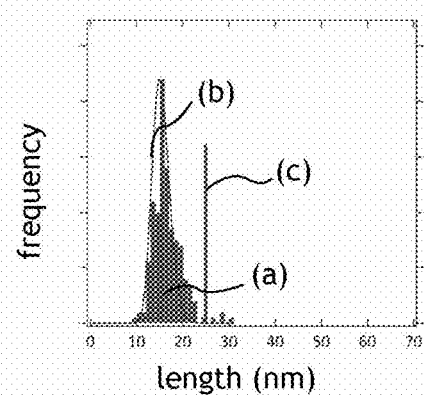
FIG. 4 illustrates the size of the magnetic nanoparticle core comprising a core and a shell.

In reference to FIG. 4, core-shell type magnetic nanoparticles 3, whose synthesis is described above, have a core 22 of mean hydrodynamic diameter essentially equal to 25 nm (illustrated by column (c) and measured by DLS) and mean length $l_0$ essentially equal to 17 nm. Columns (a) of the histogram are a measurement of the physical length of the sample nanoparticles, curve (b) is an adjustment of the distribution of nanoparticle length $l_0$ according to a log-normal law.

Figure 5:
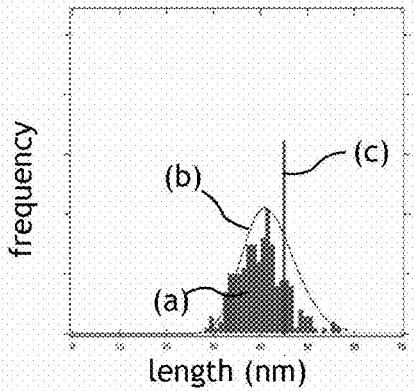
FIG. 5 illustrates the size of the magnetic nanoparticles comprising a core and a shell.

In reference to FIG. 5, core-shell magnetic nanoparticles 3, whose synthesis is described above, have a mean hydrodynamic diameter essentially equal to 45 nm (illustrated by column (c) and measured by DLS) and mean length $l_0$ essentially equal to 42 nm Columns (a) of the histogram are a measurement of the physical length of the sample nanoparticles, curve (b) is an adjustment of the distribution of nanoparticle length $l_0$ according to a log-normal law.

Figure 6:
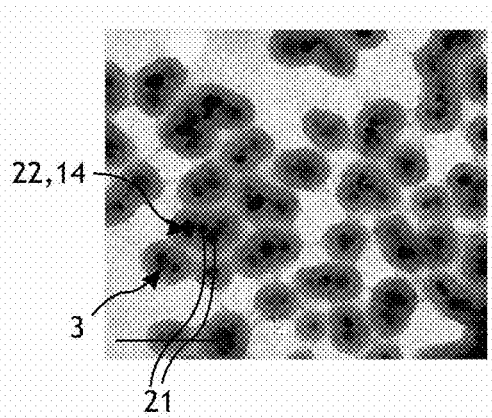
FIG. 6 is a transmission electron microscope image of magnetic nanoparticles comprising a core and a shell.

In reference to FIG. 6, the size and appearance of magnetic nanoparticles 3 may be modified. According to a preferential embodiment of the invention, the step of encapsulation in a silica shell 23 is preceded by a step of formation of an aggregate 14 of a plurality of nuclei 21 in ferromagnetic or ferrimagnetic material, by dispersion of nuclei 21 in a saline solution, so as to form core 22. Preferentially, magnetic nanoparticles 3 are dispersed in a saline solution whose ionic force is greater than or equal to 1 mM, preferentially comprised between 2 mM and 100 mM, and preferentially comprised between 4 mM and 50 mM. For example, magnetic nanoparticles 3 are dispersed in three solutions comprising ammonium chloride, at concentrations of 2 mM, 4 mM and 5 mM. FIG. 6 illustrates magnetic nanoparticles 3 produced according to a process conforming to the invention comprising a step of dispersing nuclei 21 in an NH$_4$Cl solution at a concentration of 2.5 mM. The majority of magnetic nanoparticles 3 have two or more nuclei 21. The scale bar of FIG. 1 has a length of 100 nm.

Figure 7:
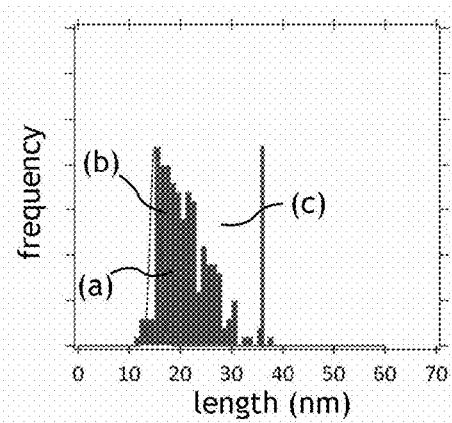
FIG. 7 illustrates the size of the magnetic nanoparticle core comprising a core and a shell.

In reference to FIG. 7, core-shell type magnetic nanoparticles 3, whose synthesis is described above, have a core 22 of mean hydrodynamic diameter essentially equal to 36 nm (illustrated by column (c) and measured by DLS) and mean length $l_0$ essentially equal to 22 nm. Columns (a) of the histogram are a measurement of the length of the sample nanoparticles, curve (b) is an adjustment of the distribution of length $l_0$ according to a log-normal law.

Figure 8:
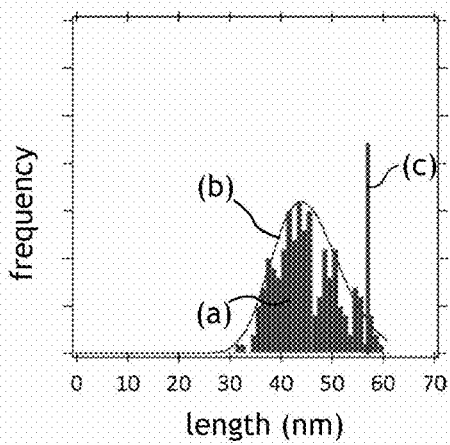
FIG. 8 illustrates the size of the magnetic nanoparticles comprising a core and a shell.

In reference to FIG. 8, core-shell type magnetic nanoparticles 3, whose synthesis is described above, have a mean hydrodynamic diameter essentially equal to 57 nm (illustrated by column (c) and measured by DLS) and mean length $l_0$ essentially equal to 44 nm. Columns (a) of the histogram are a measurement of the length of the sample nanoparticles, curve (b) is an adjustment of the distribution of length $l_0$ according to a log-normal law.

Figure 9:
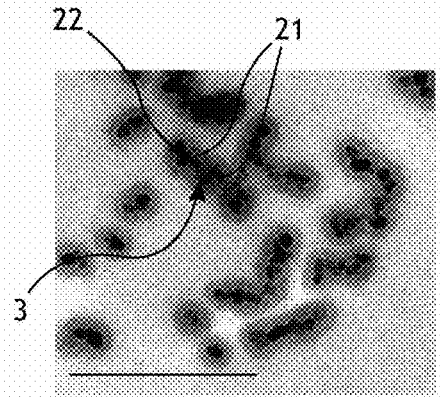
FIG. 9 is a transmission electron microscope image of magnetic nanoparticles comprising a core and a shell.

In reference to FIG. 9, magnetic nanoparticles 3 can be produced according to a process conforming to the invention comprising a step of dispersing nuclei 21 in an NH$_4$Cl solution at a concentration of 4 mM. Magnetic nanoparticles 3 and core 22 of magnetic nanoparticles 3 have an elliptical or ellipsoid shape. The length of magnetic nanoparticles 3 is 80 nm on average and the length of core 22 of magnetic nanoparticles 3 is 49 nm on average. More generally, magnetic nanoparticles 3 may have a length-to-width ratio greater than 1.5. The scale bar of FIG. 1 has a length of 200 nm.

Figure 10:
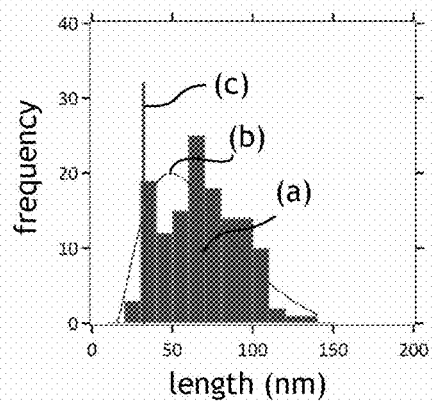
FIG. 10 illustrates the size of the magnetic nanoparticle core comprising a core and a shell.

In reference to FIG. 10, core-shell type magnetic nanoparticles 3, whose synthesis is described above, have a core 22 of mean hydrodynamic diameter essentially equal to 32 nm (illustrated by column (c) and measured by DLS) and a mean length $l_0$ essentially equal to 49 nm. Columns (a) of the histogram are a measurement of the length of the sample magnetic nanoparticles 3, curve (b) is an adjustment of the distribution of length $l_0$ of nanoparticles 3 according to a log-normal law.

Figure 11:
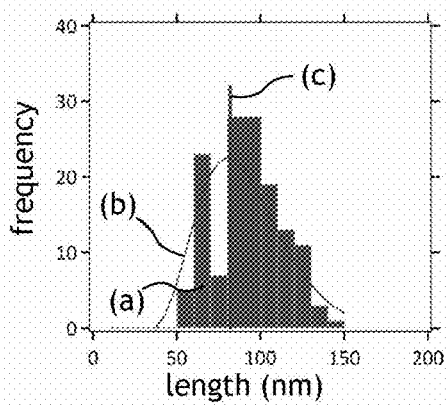
FIG. 11 illustrates the size of the magnetic nanoparticles comprising a core and a shell.

In reference to FIG. 11, core-shell type magnetic nanoparticles 3, whose synthesis is described above, have a mean hydrodynamic diameter essentially equal to 82 nm (illustrated by column (c) and measured by DLS) and a mean length $l_0$ essentially equal to 80 nm. Columns (a) of the histogram are a measurement of the length of the sample magnetic nanoparticles 3, curve (b) is an adjustment of the distribution of length $l_0$ of nanoparticles 3 according to a log-normal law.

Figure 12:
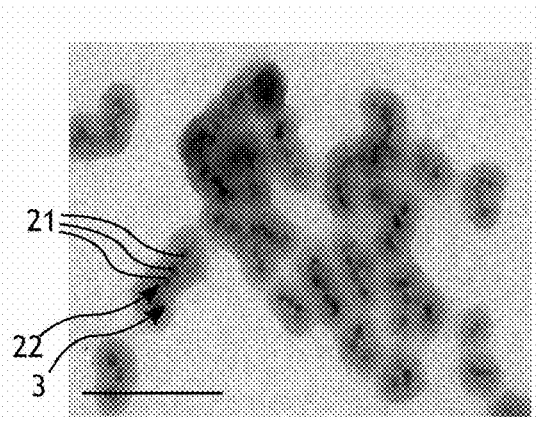
FIG. 12 is a transmission electron microscope image of magnetic nanoparticles comprising a core and a shell.

In reference to FIG. 12, magnetic nanoparticles 3 can be produced according to a process conforming to the invention comprising a step of dispersing nuclei in an NH$_4$Cl solution at a concentration of 5 mM. Magnetic nanoparticles 3 and core 22 of magnetic nanoparticles 3 have an elliptical or ellipsoid shape. The length of magnetic nanoparticles 3 is 86 nm on average and the length of core 22 of magnetic nanoparticles 3 is 55 nm on average. The scale bar of FIG. 1 has a length of 200 nm.

Figure 13:
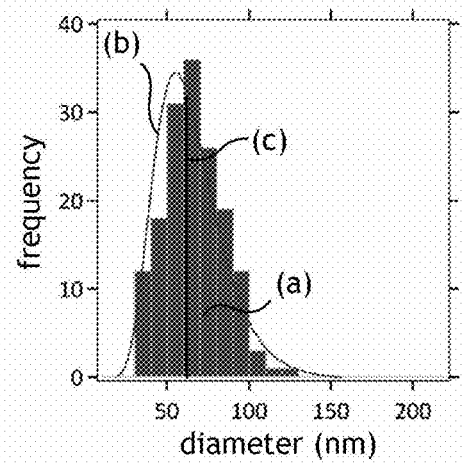
FIG. 13 illustrates the size of the magnetic nanoparticle core comprising a core and a shell.

In reference to FIG. 13, core-shell type magnetic nanoparticles 3, whose synthesis is described above, have a core 22 of mean hydrodynamic diameter essentially equal to 62 nm (illustrated by column (c) and measured by DLS) and a mean length $l_0$ essentially equal to 55 nm. Columns (a) of the histogram are a measurement of the length of the sample magnetic nanoparticles 3, curve (b) is an adjustment of the distribution of length $l_0$ of nanoparticles 3 according to a log-normal law.

Figure 14:
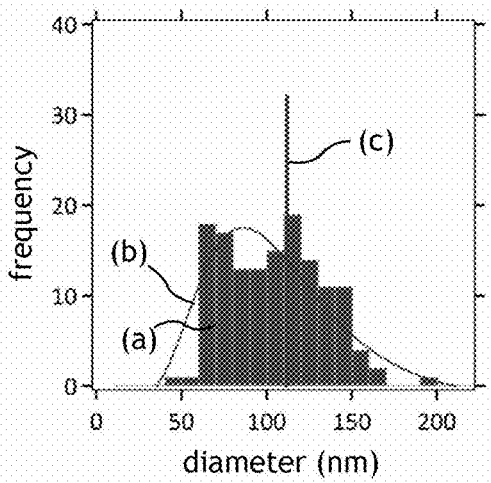
FIG. 14 illustrates the size of the magnetic nanoparticles comprising a core and a shell.

In reference to FIG. 14, core-shell type magnetic nanoparticles 3, whose synthesis is described above, have a mean hydrodynamic diameter essentially equal to 112 nm (illustrated by column (c) and measured by DLS) and a mean length $l_0$ essentially equal to 86 nm. Columns (a) of the histogram are a measurement of the length of the sample magnetic nanoparticles 3, curve (b) is an adjustment of the distribution of length $l_0$ of nanoparticles 3 according to a log-normal law.

Lengths $l_0$ of the different nanoparticles 3 presented previously are summarized in Table 1 below.

TABLE 1

| nanoparticles 3 | lengths (nm) | | [NH$_4$Cl] (mM) |
|---|---|---|---|
| | $l_0$ - core (nm) | $l_0$ - nanoparticle (nm) | |
| spherical | | | |
| A | 17 | 42 | 0 |
| B | 22 | 44 | 2.5 |
| ellipsoid | | | |
| C | 49 | 80 | 4 |
| D | 55 | 86 | 5 |

In the following description, nanoparticle 3 of types A, B, C or D means nanoparticles 3 produced, respectively, in the absence of the step of dispersing nanoparticles 3 in a saline solution of NH$_4$Cl, or in saline solutions of NH$_4$Cl preceding the encapsulation of core 22 in silica shell 23, of concentrations respectively equal to 2.5 mM, 4 mM and 5 mM.

In reference to FIG. 15, the hydrodynamic diameter of a nanoparticle 3 can be controlled by the ionic force of the saline solution in which nanoparticles 3 are dispersed before the growth step of shell 23. Columns (a), (b), (c) and (d) in FIG. 15 illustrate the mean hydrodynamic diameter of type A, B, C and D nanoparticles 3, respectively.

In reference to FIG. 16, nanoparticles 3 conforming to the invention, and preferentially nanoparticles 3 conforming to the invention comprising a core comprising an aggregate 14 of nuclei 21, can have a higher magnetization than known magnetic nanoparticles, whose core comprises a single nucleus and with no shell. Magnetization is measured in liquid phase according to the magnetic field applied. Curves (a), (b), (c) and (d) in FIG. 16 illustrate the magnetization of nanoparticles 3, of type A, B, C and D, respectively. Curve (e) illustrates the magnetization of nanoparticles whose core comprises a single nucleus and with no shell. Magnetization is measured by using a superconducting quantum interference device (SQUID) magnetometer.

In reference to FIG. 17, nanoparticles 3 conforming to the invention, and preferentially nanoparticles 3 conforming to the invention comprising a core comprising an aggregate 14 of nuclei 21, can have a higher heating power than that of known magnetic nanoparticles, whose core comprises a single nucleus and with no shell. The heating power of nanoparticles 3 caused by an alternating magnetic field is measured by using the Magnetherm device from Nanotherics. A magnetic field of 10.56 kA·m$^{-1}$ is applied at a frequency of 535 kHz onto a liquid volume of 500 µL comprising nanoparticles 3, designated by volume of ferrofluid. The volume of ferrofluid is introduced into a copper coil, which is part of a resonant RLC circuit, designed to control an AC magnetic field in a range of frequencies comprised between 300 and 550 kHz, and whose amplitude can be, for example, 10.56 kA·m$^{-1}$. The coil is cooled by water circulation so as to prevent a thermal gradient effect on the measurements. The ferrofluid volume temperature is measured by using a non-metallic fiber optic cable placed in the center of the sample. The change in the temperature measured during the experiment dT/dt is linear and the heating power SLP of nanoparticles 3 is calculated according to formula (3):

$$SLP = \frac{m_{total}}{m_{mag}} \cdot c_v \cdot \frac{dT}{dt} \quad (3)$$

where $c_v$ is the volume calorimetric capacity of water and $m_{total}$ and $m_{mag}$ are, respectively, the total mass of the sample and the mass of core 22 of nanoparticles 3. Thus, heating power SLP can be increased by using nanoparticles 3 conforming to the invention, and preferentially nanoparticles 3 in which the length of core 22 of nanoparticles 3 is greater than 20 nm. Thus, magnetic hyperthermia of nanoparticles 3, for example of type A, B, C and D illustrated by points (a), (b), (c) and (d) in FIG. 17, controlled by an alternating magnetic field permits, under predetermined conditions, reaching a temperature of the liquid in contact with nanoparticles 3 higher than by using known nanoparticles, for example illustrated by point (e) in FIG. 17. In fact, the increase in SLP with the length of the core 22 of a nanoparticle 3 can be explained by considering that a magnetic order of the core of a nanoparticle 3 is retained, during the aggregation of several nuclei 21, for example during the formation of a core 22 of generally ellipsoidal rather than spherical shape.

In reference to FIG. 18, nanoparticles 3 conforming to the invention may be used to preconcentrate, transport and release single-stranded nucleic acid target molecules 1 in solution, for example DNA or RNA molecules, in a manner controlled by magnetic hyperthermia. Generally, a plurality of single-stranded nucleic acid probe molecules 20 can be attached to nanoparticle 3, each single-stranded nucleic acid probe molecule 20 being designed to be at least partially hybridized to a single-stranded nucleic acid target molecule 1 by forming a duplex.

The capacity of a nanoparticle 3 to release single-stranded nucleic acid target molecules 1 in solution may be measured by attaching double-stranded DNA molecules to the surface of a nanoparticle 3 and then denaturing the double-stranded DNA molecules by locally heating nanoparticle 3 and/or the solution surrounding nanoparticle 3 by magnetic hyperthermia. In FIG. 18, the ratio between the quantity of single-stranded target DNA 1 released by nanoparticles 3 by magnetic hyperthermia and the initial quantity of double-stranded DNA is measured when using nanoparticles of type A or type C comparatively to denaturing by heating double-stranded DNA molecules in solution with no nanoparticles (positive control).

The double-stranded DNA molecules can be attached to nanoparticles 3 as follows. Single-stranded DNA probe molecules 18 are hybridized with single-stranded DNA target molecules 1 so as to form a duplex, in a MOPS buffer solution having an NaCl concentration equal to 0.5 M. Then, 100 equivalents of EDC and NHS are introduced in solution. A wait time of 20 minutes activates the carboxy functions of single-stranded DNA probe molecules 18. Finally, a solution comprising type A or C nanoparticles 3 is introduced into the reaction medium. EDC/NHS peptide bonds are then formed between the NH$_2$ terminations previously formed on the silica surface of the shells 23 and single-stranded DNA probe molecules 18, hybridized to single-stranded DNA target molecules 1. The number of duplexes attached to a surface is maximized. A type A nanoparticle 3 can have around 440 single-stranded DNA probe molecules 18 attached to its surface and a type C nanoparticle 3 can have around 1100 single-stranded DNA probe molecules 18 attached to its surface.

Before quantifying the number of single-stranded DNA target molecules 1 that can be released by nanoparticles 3, a positive control is created by conditioning free duplexes in a solution at a mean temperature of 95° C. for 20 min, then by quantifying the number of single-stranded DNA target molecules 1 in solution. The positive control is the "95° C." column in FIG. 1: the ratio between the number of single-stranded DNA target molecules 1 quantified in solution and the number of duplexes introduced initially is roughly equally to 100%.

Column A of the histogram illustrates a ratio essentially equal to 50% between the number of single-stranded DNA target molecules 1 quantified in solution after conditioning of type A nanoparticles 3 in an alternating magnetic field leading to magnetic hyperthermia, and the number of duplexes initially present on type A nanoparticles 3.

Column C of the histogram illustrates a ratio essentially equal to 88% between the number of single-stranded DNA target molecules 1 quantified in solution after conditioning of type C nanoparticles 3 in an alternating magnetic field leading to magnetic hyperthermia, and the number of duplexes initially present on type C nanoparticles 3.

Thus, it is possible to release, in a manner controlled by magnetic hyperthermia, a proportion greater than or equal to 50%, and preferentially greater than or equal to 80% of single-stranded DNA target molecules 1 initially present on nanoparticles 3. Preferentially, type C nanoparticles 3, and more generally the nanoparticles present in core 22 formed by an aggregate of nuclei 21, are designed, on the one hand, to have a higher quantity of duplex nucleic acids on a single nanoparticle 3 than type A nanoparticles 3 (for example, 100 DNA duplexes on average per type A nanoparticle 3 compared to 140 DNA duplexes per type C nanoparticle 3), and, on the other hand, to release a larger proportion of nucleic acids per nanoparticle.

In reference to FIG. 19, the controlled release of nucleic acid target molecules 1 by magnetic hyperthermia can be done by limiting the temperature variation of the solution comprising nanoparticles 3 to 10° C., preferentially 5° C. The curve of FIG. 19 illustrates the maintenance or limitation of the temperature of the solution comprising type C nanoparticles 3 when controlling an alternating magnetic field leading to magnetic hyperthermia of type C nanoparticles 3. Magnetic hyperthermia of nanoparticles 3 can lead to conditioning at a higher temperature than the melting temperature of the duplexes of the liquid layer surrounding nanoparticles 3, the thickness of the layer being, for example, less than 10 nm. In return, the mean temperature of the solution comprising nanoparticles 3 varies from 22° C. to 28° C. Thus, the release of nucleic acid target molecules 1 by magnetic hyperthermia conforming to the invention can be done at a mean solution temperature less than the duplex melting temperature, and preferentially at a physiological and/or ambient temperature. It is therefore possible to prevent denaturation of other biological species present in a solution to be analyzed comprising nucleic acid target molecules 1.

In reference to FIG. 20, a controlled release of single-stranded nucleic acid target molecules 1 can be done in a flow 5 of liquid 12. FIG. 20 illustrates an assembly for detecting single-stranded nucleic acid target molecules 1 comprising an electromagnet 10 with an gap 9. Electromagnet 10 may be configured as described in Lacroix, L. M., Carrey, J., & Respaud, M. (2008), *A frequency-adjustable electromagnet for hyperthermia measurements on magnetic nanoparticles*, Review of scientific instruments, 79(9), 093909. Preferentially, the width of the gap is less than 5 mm. Thus the intensity of the magnetic field controlled by electromagnet 10, evolving according to the inverse of the width of gap 9, can be adapted to lead to melting of a nucleic acid duplex 4 attached to a magnetic nanoparticle 3 by magnetic hyperthermia. The assembly also includes a microsystem 7. The microsystem 7 comprises at least one micro-channel 2 fluidically connecting with at least one entrance 24 and one exit 25. At least one part 11 of the micro-channel 2 is arranged in the gap of electromagnet 10, i.e., in the volume defined by gap 9 of electromagnet 10. As a result, the microsystem 7 is designed to be inserted into the gap of electromagnet 10. The magnetic field can, for example, be generated in an gap 9 of a width of 1.5 mm. Electromagnet core 10 can be an open low-loss ferrite ring onto which a Litz wire is wound so as to form n=55 turns. The magnetization coil may be connected to a 1 nF condenser to form an LC circuit with a resonance frequency essentially equal to 180 Hz. The resonant circuit is excited to the resonance frequency by an electric signal generator connected to an RF power amplifier, and produces, for example, a magnetic field with an amplitude of 370 Oe (measured using a single turn coil).

The micro-channel 2 can, for example, be produced by isotropic wet etching of a glass slide with a hydrofluoric acid (HF) solution. The etched slide may be superposed and sealed to another glass slide, so as to form the wall of the micro-channel 2, for example of a width of 300 μm and, for example, of a height of 50 μm. Each slide may have, for example, a thickness of 300 μm, and the total thickness of the microsystem 7 has a thickness of 600 μm. Thus, the microsystem 7 is designed to be arranged in gap 9 of electromagnet 10, the width of the gap being, for example, 1 mm. The micro-channel 2 may also be produced by using microfabrication techniques by soft photolithography, for example using microstructured PDMS layers, and/or thermo-molding techniques, for example using materials such as COC.

Electromagnet 10 comprises a magnetic core and a coil (not shown) forming a whole number n of turns around the electromagnet core. The magnetic field $H_e$ can be given by the following Formula (4):

$$H_e = \frac{n \cdot I}{W_{ag}} \quad (3)$$

where I is the intensity of the electric current in the coil. The magnetic flux Φ passing through the microsystem 7 may be given by the following Formula (4):

$$\Phi = \frac{\mu_0 \cdot n \cdot I \cdot S}{W_{ag}} \quad (4)$$

where $\mu_0$ is the magnetic permeability of the vacuum and S the surface of the turns. Thus, the magnetic field intensity may preferentially be greater than 150 G, preferentially greater than 250 G and preferentially greater than 370 G in gap 9. This magnetic field intensity is particularly designed to cause magnetic hyperthermia of magnetic nanoparticles 3 in solution.

In reference to FIG. 21, the micro-channel 2 has a part 11 arranged in gap 9 or designed to be arranged in gap 9 of electromagnet 10. FIG. 21 illustrates a top view of the micro-channel 2. The micro-channel 2 comprises an entrance 24 and an exit 25. Preferentially, the geometry of the micro-channel 2 can be optimized so that the volume defined by the micro-channel 2 is maximized in gap 9. Such an optimization may, for example, be implemented by a part 11 of the micro-channel 2 in coils in gap 9. The direction of flow 5 is illustrated by a black arrow.

In reference to FIG. 22, the magnetic hyperthermia of nanoparticles 3 can permit detecting a single-stranded nucleic acid target molecule 1.

In a step 101, nanoparticles 3 onto which are attached single-stranded nucleic acid probe molecules 18 can be introduced into a sample to be tested. The target molecules can be, in particular, microRNA molecules such as microRNA 122 molecules, whose presence can be used to diagnose liver disease such as hepatitis B and C, as well as drug-induced diseases. Single-stranded nucleic acid target molecules 1 may, during this step, hybridize onto single-stranded nucleic acid probe molecules 18 attached onto magnetic nanoparticles 3. Thus, single-stranded nucleic acid target molecules 1 present in very low concentration in a sample to be tested can be attached to the same place, i.e., onto one or more magnetic nanoparticles 3.

During a step 102 of the process, a flow 5 is generated in a liquid 12 comprising at least one magnetic nanoparticle 3. According to whether or not a pathology, or more generally a physiological event to be detected, is present, magnetic nanoparticles 3 can have on their surfaces single-stranded nucleic acid probe molecules and/or duplexes 4 formed by a single-stranded nucleic acid probe molecule 20 and a single-stranded nucleic acid target molecule 1. Flow 5 in liquid 12 can, for example, be controlled by a syringe pump or by a pressure controller between entrance 24 and exit 25 of the micro-channel 2.

During step 103 of the process, an alternating magnetic field is generated in part 11 of the micro-channel 2. This alternating magnetic field may preferentially be generated by means of electromagnet 10 described previously. The alternating magnetic field is designed to cause magnetic hyperthermia of magnetic nanoparticles 3 so as to induce denaturation of duplex(es) 4. Preferentially, the geometry of the micro-channel 2, in particular in part 11, as well as the mean flow rate of magnetic particles 3 in liquid 12 are designed so that magnetic nanoparticles 3 are transported, on average, at least 8 seconds, preferentially 9 seconds and preferentially 10 seconds, in part 11 of the micro-channel 2. This time is designated by "residence time" in part 11. In fact, the denaturation of a duplex has a minimum time, below which, at a temperature permitting denaturation of the duplex, the duplex is not yet denatured. It is therefore necessary to condition the duplex at a temperature suited to denaturation longer than this minimum, comprised between 8 and 12 seconds, preferentially comprised between 9 and 11 seconds. Thus, the geometry of the micro-channel 2 in gap 9 and the mean speed of flow 5 denatures duplexes 4 and releases single-stranded nucleic acid target molecules 1 in solution, into liquid 12 of flow 5. The mean residence time of magnetic nanoparticles 3 in flow 5 can be calculated by the following formula (5):

$$t = \frac{d \cdot h \cdot w}{v} \quad (5)$$

where d is the length of the micro-channel 2 in part 11 in the direction of flow 5, h is the height of the micro-channel 2, w is the width of the micro-channel 2 and v is the mean flow rate.

During a step 104 of the process, the single-stranded nucleic acid target molecule(s) 1 released into solution during step 103 are detected. "Detect" means performing a measurement that will show whether or not a single-stranded nucleic acid target molecule 1 is present in solution, and in particular, measure the concentration of single-stranded nucleic acid target molecules 1 in solution. The means for detecting single-stranded nucleic acid target molecules 1 are described later.

In reference to FIG. 23, the proportion of single-stranded nucleic acid target molecules 1 released into a micro-channel 2 can change with the flow rate of flow 5. FIG. 23 illustrates the proportion between the quantity of single-stranded DNA target molecules 1 released and the quantity of duplexes present on magnetic nanoparticles 3 before the magnetic field-generating step of the process. The concentration of DNA in solution is measured, for example in the step of detecting single-stranded nucleic acid target molecule(s) 1, by fluorimetry. DNA can be quantified, for example, by using a fluorimeter with an excitation wavelength of 480 nm and an emission wavelength of 520 nm, and by using a marker for single-stranded nucleic acid molecules in solution such as Oligreen (registered trademark).

Column (a) of the histogram illustrates the proportion of free single-stranded DNA in solution quantified during a negative control, in which the step of generating a magnetic field is not implemented. Column (b) of the histogram illustrates the proportion of free single-stranded DNA in solution quantified during denaturation of duplex 4 caused by heating a solution in static volume to 95° C. Column (c) of the histogram illustrates the proportion of free single-stranded DNA in solution quantified during denaturation caused by magnetic hyperthermia in static volume as described previously. Column (d) of the histogram illustrates the proportion of free single-stranded DNA in solution quantified during denaturation caused by magnetic hyperthermia according to a process conforming to the invention in a micro-channel 2 in which a flow 5 of liquid 12 comprising single-stranded nucleic acid target molecules 1 is generated at a mean flow rate of 0.11 µL·s$^{-1}$. Column (d) of the histogram illustrates the proportion of free single-stranded DNA in solution quantified during denaturation caused by magnetic hyperthermia according to a process conforming to the invention in a micro-channel 2 in which a flow 5 of liquid 12 comprising single-stranded nucleic acid target molecules 1 is generated at a mean flow rate of 0.01 µL·s$^{-1}$. Table 2 below presents the characteristics of the conditions of column (d) and column (e):

TABLE 2

| condition | d (µL · s$^{-1}$) | residence time (s) | detection volume (µL) | detection time |
| --- | --- | --- | --- | --- |
| (d) | 0.11 | 3 | 400 | 2 h 48 min |
| (e) | 0.01 | 12 | 100 | 2 h 48 min |

The proportion of DNA released under condition (d) is essentially equally to the proportion measured during the negative control. The residence time between conditions (d) and (e) is, respectively, 3 seconds and 12 seconds. Thus, it is possible to detect a release of DNA essentially equal to conditions (b) and (c) for a sufficient residence time, i.e., greater than 8 seconds, by adapting the flow rate of flow 5 for the same micro-channel 2.

In reference to FIG. 24, the detection step may be implemented by electrochemical detection. Horny et al. (Horny, M. C., Lazerges, M., Siaugue, J. M., Pallandre, A., Rose, D., Bedioui, F., . . . & Gamby, J. (2016), *Electrochemical DNA biosensors based on long-range electron transfer: investigating the efficiency of a fluidic channel microelectrode compared to an ultramicroelectrode in a two-electrode setup*, Lab on a Chip, 16(22), 4373-4381) describe a method suited to the electrochemical detection of single-stranded nucleic acid target molecules 1 in a micro-channel 2. Thus, it is possible to detect lower concentrations, for example comprised between 1 aM and 1 µM of single-stranded nucleic acid target molecules 1 in a micro-channel 2. FIG. 24 illustrates a system in which electrodes 15 are arranged in the micro-channel 2 downstream of part 11 of the micro-channel 2 relative to the direction of flow 5.

The electrodes can be arranged, for example, in the part of a glass wafer corresponding to the micro-channel 2. Thin platinum and/or titanium and/or carbon layers can be deposited, for example by a cathode sputtering deposition process, or more generally by a physical vapor deposition. Thus, a wall of the micro-channel 2 may have electrodes.

Single-stranded nucleic acid probe molecules 18 can be attached to a surface of at least one electrode 15, said single-stranded molecules being designed to be at least partially hybridized to single-stranded nucleic acid target molecule(s) 1. These single-stranded nucleic acid probe molecules 18 can be attached, for example, to an electrode layer 15 of gold or by means of thiol groups, so as to form a self-assembled layer. However, this type of layer has a relatively low maximum hybridization with single-stranded nucleic acid target molecules 1, for example, less than 15%. To this end, single-stranded nucleic acid probe molecules 18 can be preferentially attached to a thin carbon layer, for example, of amorphous type a-CNx carbon, so as to increase the maximum amount of single-stranded nucleic acid target molecules 1 hybridized.

The various electrodes 15 can be connected to one or more voltage generators, controlled by a control unit, so as to impose an electric potential difference between a working electrode 16 and a counter electrode 17.

In reference to FIG. 25, the impedance between a working electrode 16 and a counter electrode 17 depends on the state of hybridization of single-stranded nucleic acid probe molecules 18 attached on the surface of electrodes 15. In particular, the step of detecting single-stranded nucleic acid target molecules 1 dispersed in liquid 12 can be done by introducing an electrolyte containing a redox couple $Fe^{III}CN_6^{3-}/Fe^{II}CN_6^{4-}$, methylene blue as redox intercalator for the duplex, and NaCl at a concentration of 0.5 M. Curve (a) is a measurement of the impedance measured before a release of single-stranded nucleic acid target molecules 1 by magnetic hyperthermia, and curve (b) is a measurement of the impedance measured after a release of single-stranded nucleic acid target molecules 1 by magnetic hyperthermia, according to a process conforming to the invention, during which the charge transfer is facilitated by the formation of duplex 4.

The invention claimed is:

1. A process for detecting at least one single-stranded nucleic acid target molecule, comprising the steps of:
    generating a flow of a liquid in a micro-channel of a microsystem, the liquid comprising a magnetic core-shell type nanoparticle having a plurality of single-stranded nucleic acid probe molecules attached thereto, each of the plurality of single-stranded nucleic acid probe molecules being designed to be at least partially hybridized to a single-stranded nucleic acid target molecule by forming a duplex;
    generating an alternating magnetic field in a part of the micro-channel that is arranged in a gap of an electromagnet so as to cause magnetic hyperthermia in the magnetic core-shell type nanoparticle and induce denaturation of a duplex formed by one of the single-stranded nucleic acid probe molecules and by the single-stranded nucleic acid target molecule; and
    detecting the single-stranded target molecule dispersed in the liquid.

2. The process according to claim 1, wherein the micro-channel has a geometry and the flow has a mean speed such that the magnetic core-shell type nanoparticle is transported for more than 8 seconds on average in the part of the micro-channel that is arranged in the gap of the electromagnet.

3. The process according to claim 1, wherein the width $W_{ag}$ of the gap is less than 5 mm.

4. The process according to claim 1, wherein the magnetic core-shell type nanoparticle comprises a core made of ferromagnetic or ferrimagnetic material and a shell made of silica surrounding the core.

5. The process according to claim 4, wherein the core of the magnetic core-shell type nanoparticle is made of maghemite.

6. The process according to claim 4, wherein the core of the magnetic core-shell type nanoparticle has a length and width, and wherein a mean length of the core of the magnetic core-shell type nanoparticle is greater than 20 nm.

7. The process according to claim 4, wherein the core of the magnetic core-shell type nanoparticle comprises an aggregate of ferromagnetic or ferrimagnetic nuclei, the aggregate comprising on average at least two nuclei.

8. The process according to claim 4, wherein a mean length-to-width ratio of the magnetic core-shell type nanoparticle is greater than 1.5.

9. The process according to claim 1, wherein a melting temperature of the duplex is designed so that strictly more than the majority of duplexes are denatured when the alternating magnetic field is generated.

10. The process according to claim 1, wherein the step of detecting the single-stranded target molecule dispersed in the liquid is implemented by electrochemistry by imposing an electrical potential difference between two electrodes, the electrodes being partly arranged in the micro-channel.

11. The process according to claim 10, wherein the two electrodes comprise a working electrode and a counter-electrode is arranged in the micro-channel downstream of the part of the micro-channel arranged in the gap of electromagnet, in a direction of the flow.

12. The process according to claim 10, wherein the plurality of single-stranded nucleic acid probe molecules are attached to a surface of one of the electrodes.

13. The process according to claim 10, wherein one of the electrodes comprises at least one thin layer chosen from among a thin gold layer, a thin platinum layer and a thin carbon layer.

14. The process according to claim 10, wherein the liquid comprises a redox intercalator for the duplex and a redox compound couple.

15. The process according to claim 1, further comprising, prior to generating the flow of the liquid in the micro-channel of a microsystem, mixing the magnetic core-shell type nanoparticle having the plurality of single-stranded nucleic acid probe molecules attached thereto with a sample to be tested and hybridizing the plurality of single-stranded nucleic acid probe molecules with the single-stranded nucleic acid target molecule.

16. An assembly for detecting at least one single-stranded nucleic acid target molecule, the assembly comprising:
   an electromagnet with a gap,
   a micro-channel in which a liquid can flow, the micro-channel comprising at least one part arranged in the gap of the electromagnet, and
   at least one magnetic nanoparticle of the core-shell type having a plurality of single-stranded nucleic acid probe molecules attached thereto, each of the plurality of single-stranded nucleic acid probe molecules being designed to be at least partially hybridized to a single-stranded nucleic acid target molecule by forming a duplex,
   wherein the electromagnet is configured to generate an alternating magnetic field so as to cause magnetic hyperthermia of the magnetic nanoparticle when the magnetic nanoparticle is transported by the liquid into the part of the micro-channel arranged in the gap of the electromagnet and to induce a denaturation of the duplex formed by the single-stranded nucleic acid probe molecule and the single-stranded nucleic acid target molecule.

17. The assembly according to claim 16, further comprising at least two electrodes arranged at least partially in the micro-channel, and wherein a voltage difference between the at least two electrodes can be controlled to detect the single-stranded target molecule dispersed in a flow of the liquid by electrochemistry.

18. The assembly according to claim 17, further comprising single-stranded nucleic acid probe molecules attached to a surface of one of the electrodes, each single-stranded molecule being designed to be at least partially hybridized to the single-stranded nucleic acid target molecule.

19. The assembly according to claim 17, wherein one of the at least two electrodes comprises at least one thin layer chosen from among a thin gold layer, a thin platinum layer and a thin carbon layer.

* * * * *